(12) United States Patent
Krotz (10) Patent No.: US 10,496,789 B2
(45) Date of Patent: Dec. 3, 2019

(54) DISPLAY OF PRELOADED PREDICTED DATA

(71) Applicant: Dieter Krotz, Erlangen (DE)

(72) Inventor: Dieter Krotz, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 225 days.

(21) Appl. No.: 15/256,497

(22) Filed: Sep. 2, 2016

(65) Prior Publication Data
US 2018/0068064 A1 Mar. 8, 2018

(51) Int. Cl.
| | |
|---|---|
| G06F 16/51 | (2019.01) |
| G16H 10/60 | (2018.01) |
| G06T 1/20 | (2006.01) |
| G16H 30/40 | (2018.01) |
| G16H 30/20 | (2018.01) |
| G06F 19/00 | (2018.01) |
| G06F 16/58 | (2019.01) |
| G06T 1/00 | (2006.01) |

(52) U.S. Cl.
CPC ............ G06F 19/321 (2013.01); G06F 16/51 (2019.01); G06F 16/5866 (2019.01); G06T 1/0007 (2013.01); G06T 1/20 (2013.01); G16H 10/60 (2018.01); G16H 30/20 (2018.01); G16H 30/40 (2018.01); *G06T 2200/24* (2013.01); *G06T 2210/41* (2013.01)

(58) Field of Classification Search
CPC ...................................................... G06T 15/20
See application file for complete search history.

(56) References Cited

U.S. PATENT DOCUMENTS

| | | | | |
|---|---|---|---|---|
| 8,867,807 B1 * | 10/2014 | Fram | ..................... | G06F 19/321 |
| | | | | 382/128 |
| 9,042,617 B1 | 5/2015 | Reicher et al. | | |
| 2009/0052753 A1 * | 2/2009 | Sugahara | ............... | G16H 40/63 |
| | | | | 382/128 |
| 2012/0096524 A1 * | 4/2012 | Kovalan | ............... | G06F 19/321 |
| | | | | 726/5 |

OTHER PUBLICATIONS

European Search Report for related European Application No. EP 171850605, dated Feb. 14, 2018.
Viana-Ferreira, Carlos et al. "Pattern recognition for cache management in distributed medical imaging environments"; International Journal of Computer Assisted Radiology and Surgery; Springer; DE; vol. 11; No. 2; pp. 327-336; Aug. 2015.

* cited by examiner

*Primary Examiner* — Jitesh Patel
(74) *Attorney, Agent, or Firm* — Lempia Summerfield Katz LLC (57) ABSTRACT

In order to reduce a time between a user at a first computing device requesting display of a rendered volume, stored datasets or rendered volumes are preloaded at the first computing device or a second computing device in communication with the first computing device. A processor predicts which datasets are to be displayed and preloads at least one of the predicted datasets based on user-selected cases within a worklist, explicit selection by the user, or an automatic prediction by the second computing device.

20 Claims, 4 Drawing Sheets

DISPLAY OF PRELOADED PREDICTED DATA

FIELD

The present embodiments relate to predicting and preloading data to be displayed.

BACKGROUND

During volume rendering, a large amount of data (e.g., gigabytes (GBs) of data) is to be loaded from a storage drive. The storage drive may store datasets to be volume rendered and may be accessed by a number of workstations in communication with the storage drive. A user at a workstation may request retrieval and volume rendering of one of the stored datasets, and based on typical background load (e.g., for preprocessing jobs and Digital Imaging and Communications in Medicine (DICOM) receive jobs), a processor associated with the storage drive, for example, may access the dataset and/or volume render the dataset at a rate of 20-400 MB/s or less. This results in the user waiting seconds or minutes at the workstation for the volume rendered dataset to be accessed and a rendered image to be displayed at the workstation.

SUMMARY

In order to reduce a time between a user at a first computing device requesting display of an image to be rendered based on a stored dataset and the display of the image, stored datasets are preloaded at the first computing device or a second computing device in communication with the first computing device. A processor predicts which datasets are to be rendered and displayed and preloads at least one of the predicted datasets. The prediction is based on user-selected cases within a worklist, explicit selection by the user, or an automatic prediction.

In a first aspect, a method of preloading data based on which an image is to be displayed includes predicting, by a processor, at least one image dataset to be displayed. The processor retrieves the at least one image dataset from a memory in communication with the processor. The memory or another memory in communication with the memory stores the at least one image dataset. After the predicting, data identifying an image to be displayed is received. The image to be displayed corresponds to an image dataset of the at least one image dataset. The processor generates the image to be displayed. The generated image is transmitted to a computing device geographically remote from the processor or the generated image is displayed based on the received data.

In a second aspect, a method of presenting data to be displayed includes receiving, by a first computing device, first data from a second computing device. The first data indicates one or more datasets that are preloaded at the second computing device. A display of the first computing device displays a list of datasets. The list of datasets represents a first subset of datasets and a second subset of datasets. The first subset of datasets includes the one or more preloaded datasets. The first subset of datasets is represented differently than the second subset of datasets within the list of datasets. The first computing device transmits a request for a dataset of the list of datasets to the second computing device. The first computing device receives a representation of the identified dataset from the second computing device in response to the transmitting of the request for the dataset. The display of the first computing device displays the received representation of the identified dataset. A time between the transmitting of the request and the displaying of the representation of the identified dataset is less when the identified dataset is of the first subset of datasets compared to when the identified dataset is of the second subset of datasets.

In a third aspect, a system for preloading data to be displayed includes a memory configured to store a plurality of datasets, a plurality of images, or the plurality of datasets and the plurality of images. The system also includes a processor in communication with the memory. The processor is configured to predict at least one dataset of the plurality of datasets, based on which an image is to be displayed at a computing device geographically remote from the system. The processor is also configured to retrieve one or more datasets of the at least one dataset from the memory based on the prediction. The system also includes an interface in communication with the processor. The interface is configured to receive, after the prediction, data identifying a dataset of the one or more retrieved datasets from the computing device. The processor is further configured to transmit, via the interface, a representation of the identified dataset to the geographically remote computing device.

In a fourth aspect, a system for presenting data to be displayed includes an input configured to receive first data from a computing device. The first data indicates one or more datasets that are preloaded at the computing device. The computing device is geographically remote from the system. The system also includes a display in communication with the input. The display is configured to display a list of datasets. The list of datasets includes a first subset of datasets and a second subset of datasets. The first subset of datasets includes the one or more preloaded datasets. The first subset of datasets is represented differently than the second subset of datasets within the list of datasets on the display. The input is configured to receive second data. The second data identifies a dataset from the displayed list of datasets. The system further includes a processor in communication with the display. The processor is configured to transmit the received second data to the geographically remote computing device. The input is configured to receive a representation of the identified dataset from the geographically remote computing device in response to the transmission of the received second data. The display is further configured to display the received representation of the identified dataset. A time between the transmission of the received second data and the receipt of the representation of the identified dataset is less when the identified dataset from the displayed list of datasets is of the first subset of datasets compared to when the identified dataset from the displayed list of datasets is of the second subset of datasets.

DETAILED DESCRIPTION OF THE DRAWINGS

Data prediction is provided from a system point of view to load specific cases in main memory on a server side, so that when a user attempts to open a specific case, the case is already loaded in the main memory at the server. When the case is already loaded in the main memory at the server, the user waits a short period of time (e.g., less than one second) before an image generated based on the already loaded case is displayed to the user. When the case is not preloaded in the main memory at the server, the user waits a longer period of time (e.g., greater than five seconds) for the case to be loaded from a file system into the main memory.

Figure 1:
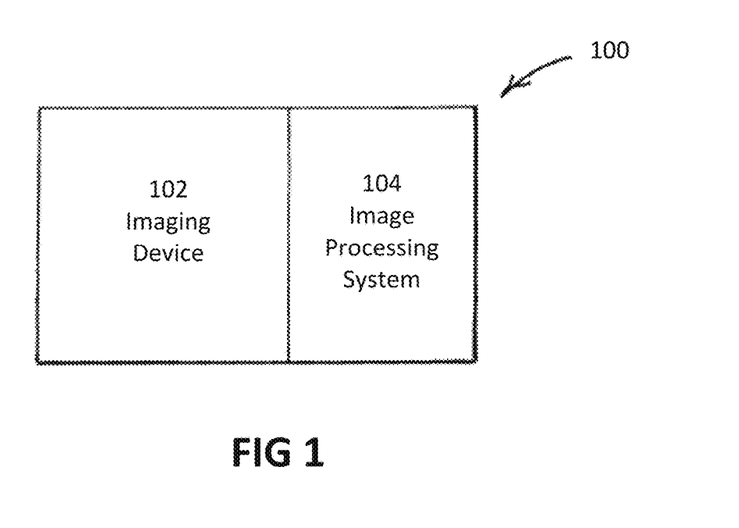
FIG. 1 shows one embodiment of an imaging system.

FIG. 1 shows one embodiment of an imaging system 100. The imaging system 100 may be used in the system and method described below. The imaging system 100 may include one or more imaging devices 102 (e.g., an imaging device) and one or more image processing systems 104 (e.g., an image processing system). Additional, different or fewer components may be provided. A dataset representing a two-dimensional (2D) or a three-dimensional (3D) (e.g., volumetric) region may be acquired using the imaging device 102 and the image processing system 104 (e.g., an imaging system). The 2D dataset or the 3D dataset may be obtained contemporaneously with the planning and/or execution of a medical treatment procedure or at an earlier time. Additional, different, or fewer components may be provided.

In one embodiment, the imaging system 100 is, for example, a CT system. The imaging system 100 may be used to create a patient model. The patient model may be used for diagnostic purposes and/or in the planning of a medical treatment procedure.

In other embodiments, the imaging system 100 may be, for example, a computed tomography (CT) system, an ultrasound system, a positron emission tomography (PET) system, and angiography system, a fluoroscopy, an x-ray system, any other now known or later developed imaging system, or any combination thereof. The imaging device 102 is a transmitter, a receiver, and/or a detector for scanning a patient. The image processing system 104 is a system or a workstation for treatment planning. The image processing system 104 may be a control processor, a renderer, a user interface processor of the imaging device 102, a separate computer, laptop, workstation, or processor, or any combination thereof. The image processing system 104 receives data representing the patient or images of the patient generated by the imaging device 102. The imaging system 100 may include more or fewer components. In one embodiment, the image processing system 104 includes a workstation and a server in communication with the workstation. Data, based on which an image to be displayed at the workstation is generated, for example, may be preloaded at the server and/or the workstation.

Figure 2:
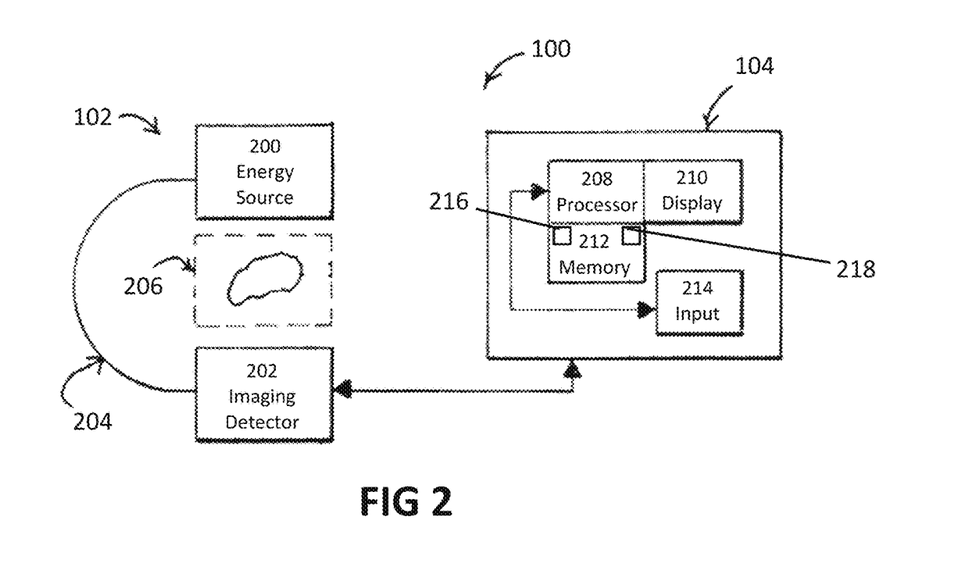
FIG. 2 shows an imaging system including one embodiment of an imaging device.

FIG. 2 shows the imaging system 100 including one embodiment of the imaging device 102. The imaging device 102 is shown in FIG. 2 as a C-arm X-ray device. The imaging device 102 may include an energy source 200 and an imaging detector 202 connected together by a C-arm 204. Additional, different, or fewer components may be provided. In other embodiments, the imaging device 102 may be, for example, a gantry-based CT device or an MRI device.

The energy source 200 and the imaging detector 202 may be disposed opposite each other. For example, the energy source 200 and the imaging detector 202 may be disposed on diametrically opposite ends of the C-arm 204. Arms of the C-arm 204 may be configured to be adjustable lengthwise, so that the energy source 200 and the imaging detector 202 may be positioned optimally in a ring structure. In certain embodiments, the C-arm 204 may be movably attached (e.g., pivotably attached) to a displaceable unit. The C-arm 204 may be moved on a buckling arm robot. The robot arm allows the energy source 200 and the imaging detector 202 to move on a defined path around the patient. During acquisition of non-contrast and/or contrast scans, for example, the C-arm 204 is swept around the patient. During the contrast scans, contrast agent may be injected intravenously. In another example, the energy source 200 and the imaging detector 202 are connected inside a gantry.

High rotation speeds may be attained with the C-arm X-ray device 102. In one embodiment, the C-arm X-ray device is operable to rotate up to 100°/s or 120°/s. In other embodiments, one complete scan (e.g., a 200 degree rotation) of the high speed C-arm X-ray device 102 may be conducted in less than 5 seconds, less than 3 seconds, less than 2 seconds, less than 1 second, less than 0.5 seconds, or less than 0.1 seconds.

The energy source 200 may be a radiation source such as, for example, an X-ray source. The energy source 200 may emit radiation to the imaging detector 202. The imaging detector 202 may be a radiation detector such as, for example, a digital-based X-ray detector or a film-based X-ray detector. The imaging detector 202 may detect the radiation emitted from the energy source 200. Data is generated based on the amount or strength of radiation detected. For example, the imaging detector 202 detects the strength of the radiation received at the imaging detector 202 and generates data based on the strength of the radiation. The data may be considered image data as the data is used to then generate an image. Image data may also include data for a displayed image.

During each rotation, the high speed C-arm X-ray device 102 may acquire between 50-500 projections, between 100-200 projections, or between 100-150 projections. In other embodiments, during each rotation, the C-arm X-ray device 102 may acquire between 50-100 projections per second, or between 50-75 projections per second. Any speed, number of projections, dose levels, or timing may be used.

A region 206 to be examined (e.g., the brain of a patient) is located between the energy source 200 and the imaging detector 202. The region 206 may be all or a portion of the patient. The region 206 may or may not include a surrounding area. For example, the region 206 to be examined may include the brain and/or other organs or body parts in the surrounding area of the brain.

The data may represent a two-dimensional (2D) or three-dimensional (3D) region, referred to herein as 2D data or 3D data. For example, the C-arm X-ray device 102 may be used to obtain 2D data or CT-like 3D data. A computer tomography (CT) device may obtain 2D data or 3D data. In another example, a fluoroscopy device may obtain 3D representation data. The data may be obtained from different directions. For example, the imaging device 102 may obtain data representing sagittal, coronal, or axial planes or distribution.

The imaging device 102 may be communicatively coupled to the image processing system 104. The imaging device 102 may be connected to the image processing system 104, for example, by a communication line, a cable, a wireless device, a communication circuit, and/or another communication device. For example, the imaging device 102 may communicate the data to the image processing system 104. In another example, the image processing system 104 may communicate an instruction such as, for example, a position or angulation instruction to the imaging device 102. All or a portion of the image processing system 104 may be disposed in the imaging device 102, in the same room or different rooms as the imaging device 102, or in the same facility or in different facilities.

All or a portion of the image processing system 104 may be disposed in one imaging device 102. The image processing system 104 may be disposed in the same room or facility as the imaging device 102. In one embodiment, the image processing system 104 and the one imaging device 102 may each be disposed in different rooms or facilities (e.g., geographically remote from each other). The image processing system 104 may represent a single image processing system or a plurality of image processing systems associated with more than one imaging device 102. For example, a plurality of workstations, at least one of which is associated with an imaging device 102, may be in communication with a geographically remote server via a network. The server may store, in a database, datasets generated by the imaging devices 102 and/or may access one or more databases outside of the server that store the datasets generated by the imaging devices 102.

In the embodiment shown in FIG. 2, the image processing system 104 includes a processor 208, a display 210 (e.g., a monitor), and a memory 212. Additional, different, or fewer components may be provided. For example, the image processing system 104 may include an input 214 (e.g., an input device and/or one or more inputs via which the image processing system 104 receives data), a printer, and/or a network communications interface.

The processor 208 is a general processor, a digital signal processor, an application specific integrated circuit, a field programmable gate array, an analog circuit, a digital circuit, an accelerated processing unit (APU), a graphics processing unit (GPU), a Manycore processor, a multicore processor, another now known or later developed processor, or combinations thereof. The processor 208 may be a single device or a combination of devices such as, for example, associated with a network or distributed processing. Any of various processing strategies such as, for example, multi-processing, multi-tasking, and/or parallel processing may be used. The processor 208 is responsive to instructions stored as part of software, hardware, integrated circuits, firmware, microcode or the like.

The processor 208 may generate an image from the data. The processor 208 processes the data from the imaging device 102 and generates an image based on the data. For example, the processor 208 may generate one or more angiographic images, fluoroscopic images, top-view images, in-plane images, orthogonal images, side-view images, 2D images, 3D representations (e.g., renderings or volumes), progression images, multi-planar reconstruction images, projection images, or other images from the data. In another example, a plurality of images may be generated from data detected from a plurality of different positions or angles of the imaging device 102 and/or from a plurality of imaging devices 102.

The processor 208 may generate a 2D image from the data. The 2D image may represent a planar slice of the region 206 to be examined. For example, the C-arm X-ray device 102 may be used to detect data that may be used to generate a sagittal image, a coronal image, and an axial image. The sagittal image is a side-view image of the region 206 to be examined. The coronal image is a front-view image of the region 206 to be examined. The axial image is a top-view image of the region 206 to be examined.

The processor 208 may generate a 3D representation (e.g., 3D reconstruction) from the data. The 3D representation illustrates the region 206 to be examined. The 3D representation may be generated from a reconstructed volume (e.g., by combining 2D images and/or by tomography) obtained by the imaging device 102 from a given viewing direction.

For example, a 3D representation may be generated by analyzing and combining data representing different planes through the patient, such as a stack of sagittal planes, coronal planes, and/or axial planes. Additional, different, or fewer images may be used to generate the 3D representation. Generating the 3D representation is not limited to combining 2D images. For example, any now known or later developed method may be used to generate the 3D representation.

The processor 208 may be a volume renderer that generates 2D projections from the reconstructed volume. The processor 208 takes color and opacity into account with a transfer function when generating the 2D projections from the reconstructed volume. Values of the reconstructed volume are converted into respective RGBA values, and the RGBA values are projected on corresponding pixels. The RGBA values may be projected on the corresponding pixels in any number of ways including, for example, volume ray casting, splatting, shear warp, photon mapping, path tracing, and/or texture-based volume rendering.

The processor 208 may display the generated images on the monitor 210. For example, the processor 208 may generate the 3D representation and communicate the 3D representation to the monitor 210. The processor 208 and the monitor 210 may be connected by a cable, a circuit, another communication coupling, or a combination thereof. The monitor 210 is a monitor, a CRT, an LCD, a plasma screen, a flat panel, a projector or another now known or later developed display device. The monitor 210 is operable to generate images for a two-dimensional view or a rendered three-dimensional representation. For example, a two-dimensional image representing a three-dimensional volume through rendering is displayed.

The processor 208 may communicate with the memory 212. The processor 208 and the memory 212 may be connected by a cable, a circuit, a wireless connection, another communication coupling, or a combination thereof. Images, data, and other information may be communicated from the processor 208 to the memory 212 for storage, and/or the images, the data, and the other information may be communicated from the memory 212 to the processor 208 for processing and/or routing to the display 210. For example, the processor 208 may communicate the generated images, image data, or other information to the memory 212 for storage.

The memory 212 is a computer readable storage media (e.g., non-transitory computer-readable storage media). The computer readable storage media may include various types of volatile and non-volatile storage media, including but not limited to random access memory, read-only memory, programmable read-only memory, electrically programmable read-only memory, electrically erasable read-only memory, flash memory, magnetic tape or disk, optical media and the like. The memory 212 may be a single device or a combination of devices. The memory 212 may be adjacent to, part of, networked with and/or remote from the processor 208.

In one embodiment, the memory 212 includes a main memory 216 and another memory 218 including a database. The main memory 216 and the other memory 218 may be part of a same computing device (e.g., the server) or may be included in separate computing devices, respectively (e.g., the server and another computing device geographically remote from the server). The database may store datasets and/or images in the Digital Imaging and Communications in Medicine (DICOM) format.

The input 214 may include one or more input devices configured to allow a user to interact with any components of the image processing system 104. The one or more input devices 214 may include a number pad, a keyboard, a cursor control device such as, for example, a mouse or a joystick, a touch screen display, a remote control, or any other device operative to interact with the image processing system 104.

The image processing system 104 (e.g., the input 214) may include one or more input and/or output interfaces via which data is received and/or sent. The one or more input devices 214 may be in communication with the processor 208 and the memory 212, for example, via the one or more interfaces. For example, a first computing device (e.g., a workstation) of the image processing system 104 and a second computing device (e.g., a server) of the image processing system 104 may be in communication via respective interfaces.

Figure 3:
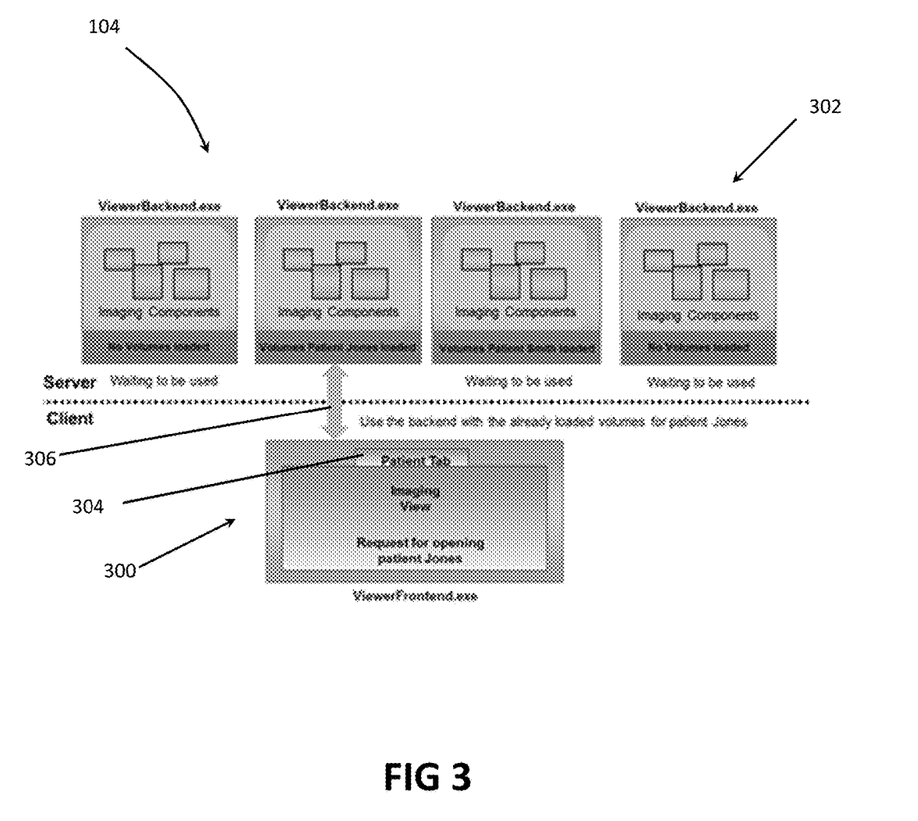
FIG. 3 shows one embodiment of an image processing system.

FIG. 3 shows one embodiment of an image processing system 104 including a first computing device 300 in communication with a second computing device 302. In one embodiment, the first computing device 300 is a workstation, and the second computing device 302 is a server. The server 302 may, for example, be geographically remote from the workstation 300. For example, the workstation 300 may be within a hospital in which imaging devices used to generate image datasets are located, and the server 302 may be in a different room within the hospital, may be in a different building within the hospital, may be in a different building outside of the hospital, may be in a different city, may be in a different state, or may be in a different country.

The workstation 300 and the server 302 may each include a respective memory and processor. In one embodiment, the server 302 includes the main memory 216, in which preloaded datasets are stored. The server 302 may also include the other memory 218 including the database, or the other memory 218 is external to and in communication with the server 302. In another embodiment, the workstation 300 includes the main memory 216 and/or the other memory 218, which includes the database. Preloading datasets may include downloading the datasets from the database of the other memory 218, for example, to the main memory 216. The time this downloading takes may be affected by network bandwidth, bus bandwidth, hardware parameters (e.g., hard drive speed), another parameter, or any combination thereof.

A doctor or a nurse (e.g., a user), for example, uses the workstation 300 to access image datasets and/or rendered images (e.g., volumes) preloaded at or provided through the server 302 and/or to access image datasets stored in the other memory 218. The workstation 300 runs a graphical user interface (GUI) through which the user may request and/or view a list of image datasets stored at the server 302 and/or the other memory 218, and/or through which the user may view images generated based on one of the image datasets. The GUI running on the workstation 300 may include patient-specific tabs 304, for example, that allow the user to move between viewing images for different patients. As discussed below, the workstation 300 may send a request 306 to the server 302 to view a representation of at least one image dataset already loaded at the server 302. As illustrated in FIG. 3, image datasets (e.g., volumes) representing at least a portion of "Patient Jones" and datasets representing at least a portion of "Patient Smith" are already loaded. The datasets being preloaded at the server 302 decreases the time between the user request for an image at the workstation 300 and the server 302 rendering and sending the image to the workstation 300 for display, compared to the server 302 having to access memory within or outside of the server 302 to load and render an image dataset in response to the user request.

Figure 4:
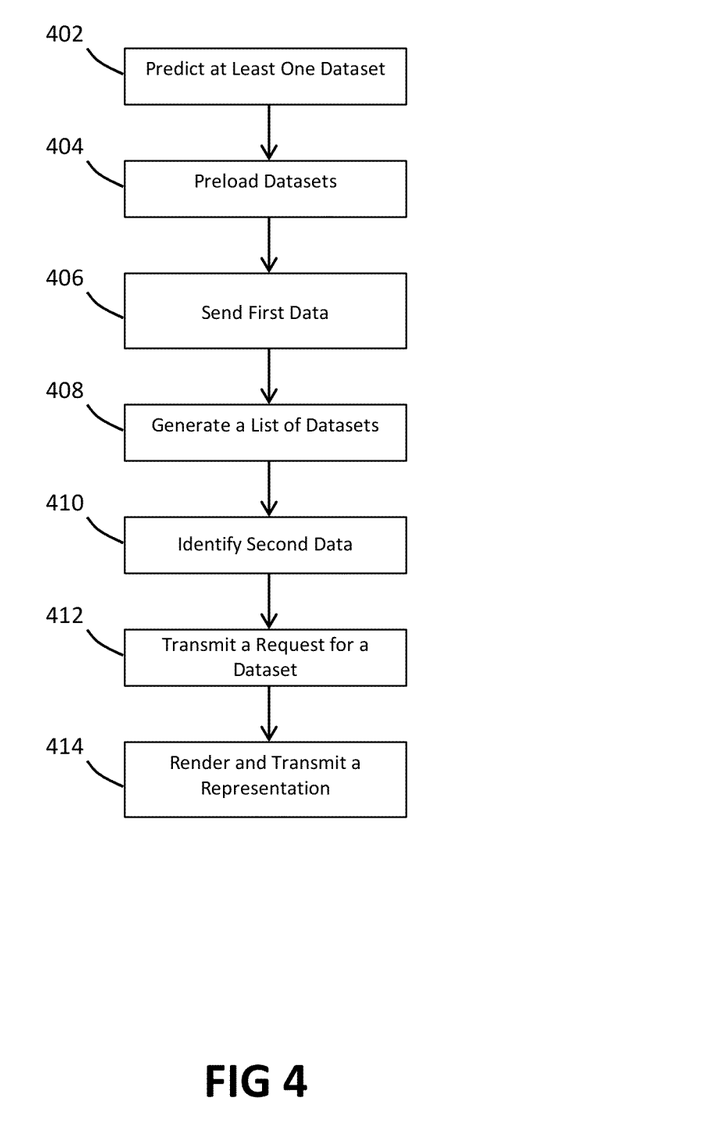
FIG. 4 shows a flowchart of an example of a method for preloading and displaying data.

FIG. 4 shows a flowchart of one embodiment of a method 400 for preloading data (e.g., image data, a dataset, an image dataset), based on which an image is to be displayed. The image data may, for example, be CT image data or image data generated during rotation of a C-arm during X-ray imaging. Alternatively, the image data may be generated with another imaging device such as, for example, an MRI device. The method may be performed using the imaging system 100 shown in FIGS. 1 and 2 (e.g., at least some of the acts of the method may be performed by the processor 208) or another imaging system. For example, the acts of the method are implemented by one or more processors using instructions from one or more memories. The method is implemented in the order shown, but other orders may be used. Additional, different, or fewer acts may be provided. Similar methods may be used for preloading image data.

The method 400 is performed by a first computing device (e.g., a workstation) and a second computing device (e.g., a server) in communication with the workstation. The workstation may be in communication with the server, for example, via a communication line, a cable, a wireless device, a communication circuit, a network, and/or another communication device. An embodiment of the method 400 may be performed by a single computing device.

The workstation and the server may each include a processor, a display (e.g., a monitor), and a memory. Additional, different, or fewer components may be provided. For example, the workstation and the server may each include an input device and/or a network communications interface. In one embodiment, the workstation and/or the server form at least part of the image processing system 104 of FIGS. 1-3, and each of the workstation and the server may include at least a processor (e.g., the processor 208), a memory (e.g., the memory 212), an input (e.g., the input 214), and an interface.

The memory of the server stores a plurality of image datasets. The plurality of image datasets correspond to different volumes of a single patient, volumes of different patients, datasets generated using different imaging devices, or any combination thereof. The plurality of image datasets may be generated with the imaging device 102 of FIGS. 1 and 2 and/or one or more other imaging devices. In one embodiment, another memory (e.g., memory of a file system or a database) in communication with the memory of the server (e.g., main memory) stores the plurality of image datasets, and the memory of the server stores preloaded (e.g., retrieved) image datasets and/or representations (e.g., images or rendered volumes) generated based on image datasets. The memory of the server and/or the other memory may store image datasets, as generated by one or more imaging devices, and/or rendered volumes.

In act 402, a processor of the server (e.g., the server 302) predicts at least one dataset to be stored (e.g., loaded) in a memory of the server or another computing device (e.g., in communication with the server) for future rendering and transmission of an image for display at the workstation (e.g., the workstation 300).

In a first embodiment (e.g., batch mode prediction), the processor of the server predicts which dataset of a plurality of datasets stored in the memory of the server, one or more other memories, or any combination thereof is to be used for future image rendering and display of the rendered image at the workstation based on data received from the workstation or otherwise accessed (e.g., retrieved from the workstation by the server). For example, a user of the workstation may select, with an input device (e.g., a mouse and a keyboard), one or more cases (e.g., corresponding to one or more datasets to be displayed) on which the user plans to work. The user may select cases (e.g., corresponding to datasets to be displayed) within a worklist. The worklist may be displayed and cases within the worklist may be selected via, for example, a browser application and/or any other external worklist viewing applications. The selected cases may represent a number of cases the user (e.g., a nurse or doctor) plans on working on over a predetermined amount of time. For example, a doctor may select five cases the doctor plans on reviewing before lunch or before leaving for the day.

The workstation transmits data identifying the selected cases (e.g., corresponding to datasets) to the server. The processor of the server, upon receipt of the data identifying the selected cases, predicts the at least one dataset to be displayed based on the received data. The data identifying the selected cases may identify an order in which the user plans to review the cases. Alternatively, the processor of the server may predict an order in which the user plans to review the cases. For example, the processor may order the selected cases based on an order in which the user selected the cases within the worklist, dates/times the datasets were created, the dataset the user most recently reviewed (e.g., a CT dataset for "Patient Jones"), another parameter, or any combination thereof.

In a second embodiment (e.g., manual prediction), the processor of the server again predicts the datasets based on data received from the workstation. The user, instead of selecting cases within a worklist, however, may identify a group of cases (e.g., corresponding to datasets) to be preloaded via a command within the GUI. In other words, the user may explicitly trigger the loading of the datasets on the server. The workstation transmits data identifying the group of cases (e.g., corresponding to datasets) explicitly selected by the user to the server. The processor of the server, upon receipt of the data identifying the explicitly selected cases, predicts the at least one dataset to be used for future image rendering and display of the rendered image at the workstation based on the received data. The second embodiment, manual prediction mode, may be useful for sessions where different users (e.g., different doctors, nurses, or any combination thereof) are reviewing specific cases (e.g., Oncology Board). Before a review session, the specific cases may be preloaded manually, which is further discussed below.

In a third embodiment (e.g., automatic prediction), the processor of the server automatically predicts which datasets are to be used for future image rendering and display of the rendered image at the workstation. In one example, the server is in communication with a plurality of workstations. The processor of the server analyzes user worklist entries for all users of the respective workstations. The processor may determine the first N entries in the worklists (e.g., corresponding to datasets stored in the memory of the server) until a maximum number of preloaded cases is achieved. The maximum number of preloaded cases may be based on a maximum storage space available (e.g., 72 GB). In another embodiment, the processor of the server analyzes study dates/times for datasets that are stored in the memory of the server, for example. The processor predicts that the datasets with most recent dates/times will be rendered displayed at the workstation. In yet another embodiment, the processor of the server uses a neural network that is trained with behaviors of the user to predict datasets to be rendered and displayed at the workstation. The processor of the server may predict the datasets to be rendered and displayed at the workstation based on outputs of the neural network.

In act 404, the memory of the server preloads at least some datasets of the at least one dataset predicted in act 402.

One or more datasets of the at least one dataset may be a 3D dataset. The 3D dataset may be multiple gigabytes in size or larger. A redundant array of independent disks (RAID) system (e.g., part of the image processing system 104 as part of the server or separate from the server) may store some or all of the datasets to be preloaded at the server. A RAID system of a radiology department, for example, with a typical background load (e.g., preprocessing jobs, DICOM receive jobs) may be operable at a 20-50 MB/s data transfer rate. When the RAID system is idle, the RAID system may be operable at 100-400 MB/s. In other scenarios, the RAID system may be operable at less than 20 MB/s. Accordingly, the memory of the server may take minutes to preload the 3D dataset.

For the first prediction embodiment discussed above, the batch mode prediction, the processor and the memory of the server may preload a first dataset of the predicted datasets. The processor and memory may not start the process of preloaded a second dataset of the predicted datasets until the first dataset is rendered and transmitted to the workstation in act 414 discussed below. For the second and third prediction embodiments discussed above, the manual prediction and the automatic prediction, the processor and the memory of the server may preload at least a portion of the predicted datasets in parallel or in series, and the processor of the server may preload additional datasets of the predicted datasets when storage space becomes available. Other approaches preloading any number of datasets before or after transmission and/or memory availability may be used.

In one embodiment, only a portion of the memory is reserved for storing preloaded data (e.g., one or more datasets). For example, 20% percent of storage space of the memory may be reserved for storing preloaded datasets (e.g., one or more datasets). This percentage of storage space may be defined as a maximum storage space to be used for preloaded data. Other percentages of storage space may be reserved.

If the maximum storage space is reached, the processor of the server may wait until a large enough portion of the memory of the server is available to preload the next dataset based on the predicted datasets. Once the user of the workstation, for example, requests an image based on a preloaded dataset from the server, receives the rendered image, and closes the rendered image, the processor of the server may delete the preloaded dataset from the memory of the server, for example. In one embodiment, one preloaded dataset is not deleted from the memory of the server, for example, until another preloaded dataset is transmitted from the server to the workstation. Storage space may thus be freed, allowing additional preloaded data to be stored in the memory of the server.

In act 406, the server sends first data to the workstation, and the workstation receives the first data. The first data identifies one or more datasets that are loaded (e.g., generated or rendered) at the server. For example, the first data indicates that the at least one dataset preloaded in act 404 is available in the server. In one embodiment, the server sends the first data after the memory of the server, for example, has preloaded the dataset. In another embodiment, the server does not send the first data until all datasets of a group of datasets (e.g., all datasets of the at least one dataset) to be preloaded have been stored (e.g., loaded) in the memory of the server. In the third prediction embodiment discussed above, the computing device sends the first data to the workstation without receiving any requests for datasets to be preloaded from the workstation.

In act 408, the processor of the workstation generates a list of datasets, and the display of the workstation displays the generated list within the GUI. The list of datasets may correspond to the worklist, may include a number of most recent datasets generated for the patient and/or using a particular imaging device, or another subset of the datasets. The datasets represented within the list of datasets displayed at the workstation may be stored in the memory of the server, another memory, or a combination thereof.

Figure 5:
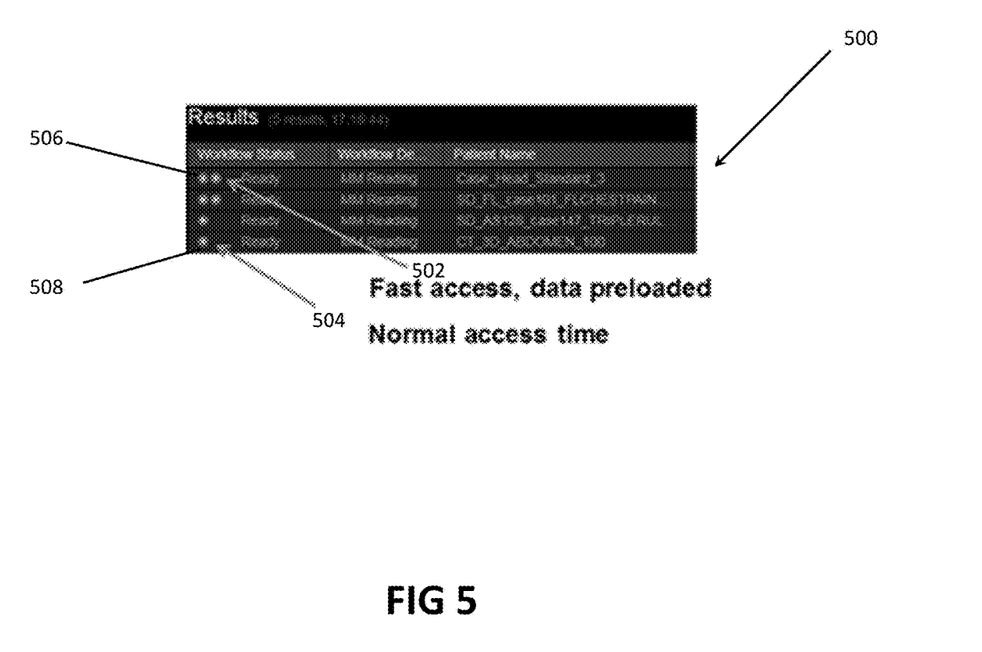
FIG. 5 illustrates one embodiment of a list of datasets that may be displayed at the first computing device.

FIG. 5 illustrates one embodiment of a list 500 of datasets that may be displayed at the workstation. The list 500 may include different information that identifies, for example, a patient that was imaged, a body part that was imaged, an imaging device used, and/or other information. The list 500 may represent the worklist the user plans to work through.

The list 500 may include a first subset of datasets 502 and a second subset of datasets 504. The first subset of datasets 502 may be datasets that have been preloaded at the server, and the second subset of datasets 504 may be datasets that have not been preloaded at the server. The first subset of datasets 502 may be represented differently than the second subset of datasets 504. As shown in the example of FIG. 5, datasets of the first subset of datasets are identified with two icons 506, while the datasets of the second subset of datasets 504 are identified with a single icon 508. Datasets that have been preloaded at the server may be identified within the list 500 in any number of other ways including, for example, with different colors, with different icons, with additional icons, with different text, as a separate list, or any combination thereof.

In act 410 of FIG. 4, the processor of the workstation identifies second data. The second data identifies one or more datasets (e.g., a dataset) from the list of datasets displayed in act 410. The processor of the workstation may identify the second data based on a user input such as, for example, a mouse and/or a keyboard of the workstation. For example, the user of the workstation may select a dataset from the list of datasets displayed on the display of the workstation. The processor of the workstation generates the second data, which identifies the selected dataset from the list of datasets, based on a location within the GUI the user clicked using, for example, the mouse.

In act 412, the workstation transmits a request for the dataset(s) selected in act 410 to the server based on the second data. In act 414, the processor of the server renders a representation of the selected dataset (e.g., an image generated from the selected dataset), and the server transmits the rendered representation of the selected dataset to the workstation. The processor may generate or render the representation of the selected dataset based on additional information sent by the user via the workstation and received by the server. The information may include, for example, an orientation of the representation of the selected dataset and/or a direction from which the representation of the selected dataset is viewed. The processor of the server, in act 414, may generate a 2D projection of the 3D dataset using volume rendering and/or may generate a 3D image based on the 3D dataset. The transmitted image from the selected dataset is received by the workstation and displayed by the display of the workstation.

When the user selects, in act 410, a dataset within the generated list of datasets displayed at the workstation that has already being preloaded, a time between the transmission of the request from the workstation to the server in act 414 and the receipt of the representation of the second dataset in act 416 is less compared to when the user selects a dataset within the generated list that has not been pre-loaded. This time difference may be seconds, minutes, or hours depending on the dataset to be loaded. With the present embodiments, the user (e.g., the doctor) may not waste time waiting for volumes to be loaded and/or rendered at a workstation, allowing the user to more efficiently work.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method of preloading data based on which an image is to be displayed, the method comprising:
predicting, by a processor, at least one image dataset to be displayed from a plurality of datasets;
preloading, by the processor, the at least one image dataset from a first memory in communication with the processor based on the predicting, the preloading comprising receiving, by a second memory in communication with the first memory, the at least one predicted image dataset from the first memory and storing, by the second memory, the at least one predicted image dataset;
sending display data to a display device for displaying a list of the plurality of datasets, the display data indicative of whether each dataset of the plurality of datasets is preloaded, such that when the list of the plurality of datasets is displayed, the preloaded at least one image dataset is depicted differently in the displayed list than non-preloaded datasets of the plurality of datasets;
receiving, after the predicting, data identifying an image to be displayed, the image to be displayed corresponding to an image dataset of the preloaded at least one image dataset;
generating, by the processor, the image to be displayed; and
transmitting the generated image to a computing device geographically remote from the processor or displaying the generated image based on the received data.

2. The method of claim 1, wherein the preloaded at least one image dataset stored in the second memory is at least one dataset of the plurality of datasets stored in the first memory.

3. The method of claim 2, wherein the plurality of datasets are image datasets representing volumes of one or more patients.

4. The method of claim 2, wherein the data identifying the image is first data, and
wherein predicting the at least one image dataset to be displayed comprises:
receiving second data from the computing device; and
identifying the at least one image dataset to be displayed based on the received second data.

5. The method of claim 4, wherein the received second data comprises a list identifying an order of image datasets to be displayed.

6. The method of claim 5, wherein preloading the at least one image dataset comprises preloading a first image dataset from the plurality of datasets stored in the first memory, the first image dataset being first in the order of the list, the generated image being a first image generated based on the first image dataset, and
wherein the method further comprises preloading a second image dataset from the plurality of datasets stored in the first memory after the first image is transmitted to the geographically remote computing device or displayed, the second image dataset being second in the order of the list.

7. The method of claim 6, further comprising:
generating, by the processor, a second image to be displayed based on the second image dataset;
transmitting the generated second image to the geographically remote computing device or displaying the generated second image; and
deleting, by the processor, the first image dataset.

8. The method of claim 4, wherein the received second data comprises a plurality of requests from the geographically remote computing device, the plurality of requests identifying a number of image datasets of the plurality of datasets stored in the first memory.

9. The method of claim 8, wherein preloading the at least one image dataset comprises preloading one or more image datasets of the image datasets identified by the plurality of requests from the first memory.

10. The method of claim 1, wherein predicting the at least one image dataset comprises automatically identifying, by the processor, the at least one image dataset to be displayed.

11. A method of presenting data to be displayed, the method comprising:
receiving, by a first computing device, first data from a second computing device, the first data indicating one or more datasets that are preloaded and stored at the second computing device based on a prediction of the one or more datasets to be displayed;
displaying, by a display of the first computing device, a list of datasets, the list of datasets representing a first subset of datasets and a second subset of datasets, the first subset of datasets comprising the one or more preloaded datasets, the first subset of datasets being depicted differently in the displayed list of datasets than the second subset of datasets within the displayed list of datasets;
transmitting, by the first computing device, a request for a dataset of the displayed list of datasets to the second computing device;
receiving, by the first computing device, a representation of the requested dataset from the second computing device in response to the transmitting of the request for the dataset; and
displaying, by the display of the first computing device, the received representation of the requested dataset,
wherein a time between the transmitting of the request and the displaying of the representation of the requested dataset is less when the requested dataset is of the first subset of datasets compared to when the requested dataset is of the second subset of datasets.

12. The method of claim 11, further comprising:
receiving, by the first computing device, second data, the second data identifying the dataset of the request from the displayed list of datasets, the transmitting of the request comprising transmitting the request in response to the received second data; and
receiving, by the first computing device, third data, the third data identifying at least one dataset to be displayed, the at least one dataset to be displayed being at least one dataset of a plurality of datasets stored in a memory geographically remote from the first computing device and comprising the one or more preloaded datasets.

13. The method of claim 12, wherein receiving the second data comprises receiving the second data from a user via an input device, and
wherein receiving the third data comprises receiving the third data from the user or another user via the input device or another input device.

14. The method of claim 12, wherein the at least one dataset to be displayed includes a first dataset and a second dataset,
wherein the received first data indicates that the first dataset is preloaded at the second computing device,
wherein the received second data identifies the first dataset from the displayed list of datasets,
wherein receiving the representation of the identified dataset comprises receiving, by the first computing device, a representation of the first dataset from the second computing device in response to the transmitting of the received third data, and
wherein after the receiving of the representation of the first dataset, the method further comprises receiving, by the first computing device, fourth data from the second computing device, the fourth data indicating that the second dataset is preloaded at the second computing device.

15. The method of claim 11, wherein the received first data indicates that a plurality of datasets are preloaded at the second computing device.

16. The method of claim 11, wherein the first subset of datasets is depicted differently in the displayed list of datasets than the second subset of datasets in that, within a graphical user interface displayed by the display of the first computing device, depictions for datasets of the first subset of datasets within the displayed list are different colors, have different icons, have additional icons, have different text, or any combination thereof compared to depictions for datasets of the second subset of datasets within the displayed list.

17. The method of claim 11, wherein receiving the first data comprises receiving the first data from the second computing device without any request for the one or more datasets to be preloaded being sent from the first computing device to the second computing device.

18. A system for preloading data to be displayed, the system comprising:
a memory configured to store a plurality of datasets, a plurality of images, or the plurality of datasets and the plurality of images;
a processor in communication with the memory, the processor configured to:
predict at least one dataset of the plurality of datasets, based on which an image is to be displayed at a computing device geographically remote from the system; and
preload one or more datasets of the at least one dataset from the memory based on the prediction; and
an interface in communication with the processor, the interface configured to:
transmit, to a display device in communication with the interface, display data for displaying a list of the plurality of datasets, the display data indicating that when the list of the plurality of datasets is displayed the one or more preloaded datasets are depicted differently in the displayed list than non-preloaded datasets of the plurality of datasets; and
receive, after the prediction, data identifying a dataset of the one or more preloaded datasets from the computing device, wherein the processor is further configured to transmit, via the interface, a representation of the identified dataset to the geographically remote computing device, and wherein another memory is configured to store the one or more datasets preloaded based on the prediction.

19. The system of claim 18, wherein less than all storage capacity of the second memory is allocated for storage of preloaded datasets.

20. A system for presenting data to be displayed, the system comprising:

an interface configured to receive first data from a computing device, the first data indicating one or more datasets that are preloaded and stored at the computing device based on a prediction of the data to be displayed, the computing device being geographically remote from the system;

a display in communication with the input, the display configured to display a list of datasets, the list of datasets comprising a first subset of datasets and a second subset of datasets, the first subset of datasets comprising the one or more preloaded datasets, the first subset of datasets being depicted differently in the displayed list of datasets than the second subset of datasets within the displayed list of datasets on the display, wherein the input is configured to receive second data, the second data identifying a dataset from the displayed list of datasets;

a processor in communication with the display, the processor configured to transmit the received second data to the geographically remote computing device, wherein the input is configured to receive a representation of the identified dataset from the geographically remote computing device in response to the transmission of the received second data, wherein the display is further configured to display the received representation of the identified dataset, and wherein a time between the transmission of the received second data and the receipt of the representation of the identified dataset is less when the identified dataset from the displayed list of datasets is of the first subset of datasets compared to when the identified dataset from the displayed list of datasets is of the second subset of datasets.

* * * * *